(12) United States Patent
Sun et al.

(10) Patent No.: US 10,927,062 B1
(45) Date of Patent: Feb. 23, 2021

(54) METHOD FOR TREATING OXYGENATED VOLATILE ORGANIC COMPOUNDS IN FISCHER-TROPSCH SYNTHESIS REACTION WATER

(71) Applicant: YANKUANG ENERGY R&D CO., LTD., SHANGHAI, Shanghai (CN)

(72) Inventors: Qiwen Sun, Shanghai (CN); Zhengwei Yang, Shanghai (CN); Jisen Liu, Shanghai (CN); Zongsen Zhang, Shanghai (CN); Xiaojiang Zhou, Shanghai (CN)

(73) Assignee: YANKUANG ENERGY R&D CO., LTD., SHANGHAI, Shanghai (CN)

( * ) Notice: Subject to any disclaimer, the term of this patent is extended or adjusted under 35 U.S.C. 154(b) by 0 days.

(21) Appl. No.: 16/887,809

(22) Filed: May 29, 2020

(30) Foreign Application Priority Data

Nov. 12, 2019 (CN) .......................... 201911101791.6

(51) Int. Cl.
| | | |
|---|---|---|
| *C07C 29/136* | (2006.01) | |
| *C02F 101/34* | (2006.01) | |
| *C10G 2/00* | (2006.01) | |
| *B01D 3/14* | (2006.01) | |
| *C02F 101/32* | (2006.01) | |
| *C02F 1/04* | (2006.01) | |

(52) U.S. Cl.
CPC ............ *C07C 29/136* (2013.01); *B01D 3/143* (2013.01); *C02F 1/04* (2013.01); *C02F 2101/322* (2013.01); *C02F 2101/34* (2013.01); *C10G 2/32* (2013.01); *C10G 2300/1022* (2013.01)

(58) Field of Classification Search
CPC ................... C07C 29/136; C10G 2/32; C10G 2300/1022; C02F 1/04; C02F 2101/322; C02F 2101/34; B01D 3/143

See application file for complete search history.

(56) References Cited

FOREIGN PATENT DOCUMENTS

| CN | 101492332 A | 7/2009 |
|---|---|---|
| CN | 101492360 A | 7/2009 |
| CN | 101555194 A | 10/2009 |
| CN | 102060660 A | 5/2011 |
| CN | 102442882 A | 5/2012 |
| CN | 103044217 A | 4/2013 |

*Primary Examiner* — Jafar F Parsa
(74) *Attorney, Agent, or Firm* — Hamre, Schumann, Mueller & Larson, P.C.

(57) ABSTRACT

The invention relates to a method for treating oxygenated volatile organic compounds in Fischer-Tropsch synthesis reaction water. Fischer-Tropsch synthesis reaction water is subjected to (a) primary concentration and separation, (b) carbonyl compound hydrogenation, (c) carbonyl compound cutting, (d) mixed-alcohol dehydration, (e) solvent recovery, (f) ethyl alcohol separation, (g) methyl alcohol removal and separation, (h) isopropanol separation, (i) propyl alcohol cutting, (j) n-propyl alcohol separation, and (k) 2-butanol separation, so that basic organic chemicals such as ethyl alcohol, isopropanol, n-propyl alcohol, 2-butanol and mixed alcohols are obtained. Compared with the prior art, the method directly converts the concentrated Fischer-Tropsch synthesis water rich in alcohols, aldehydes, ketones, acids, and esters into a mixed-alcohol solution by hydrogenation, thus having the advantages of simple separation process and high product purity.

11 Claims, 1 Drawing Sheet

METHOD FOR TREATING OXYGENATED VOLATILE ORGANIC COMPOUNDS IN FISCHER-TROPSCH SYNTHESIS REACTION WATER

BACKGROUND OF THE INVENTION

1. Technical Field

The invention relates to the technical field of Fischer-Tropsch synthesis, in particular to a method for treating oxygenated volatile organic compounds in Fischer-Tropsch synthesis reaction water.

2. Description of Related Art

Fischer-Tropsch synthesis is a technique for converting synthesis gas ($CO+H_2$) into liquid fuels and chemicals by chemical methods. Synthetic fuel oil is a clean fuel that does not contain sulfuric, nitric or aromatic compounds. With the reduction of international oil-gas resources, changes of the market condition, and the requirements for environmental friendliness, the development and industrialization of coal and natural gas liquefaction technologies based on Fischer-Tropsch synthesis are being of greater and greater significance for guaranteeing the security of national energy supply and realizing energy conservation and emission reduction.

In the reaction process of Fischer-Tropsch synthesis, most oxygen atoms in CO are converted into water, and only a small part of oxygen atoms are converted into oxygenated volatile organic compounds that can be dissolved in water, and hence water separated out of a Fischer-Tropsch synthesis reactor normally contains a certain quantity of oxygenated volatile organic compounds, wherein the concentration and composition of oxygenated volatile organic compounds in reaction water depend on the process condition of Fischer-Tropsch synthesis and the types of catalysts. Generally, the concentration of oxygenated volatile organic compounds in low-temperature Fischer-Tropsch synthesis reaction water is about 3%, and the concentration of oxygenated volatile organic compounds in high-temperature Fischer-Tropsch synthesis reaction water is about 10%. Industrial devices for Fischer-Tropsch synthesis are usually have a large size. The separation and purification of oxygenated volatile organic compounds in reaction water will increase the economic benefits of enterprises.

From the perspective of separation, Fischer-Tropsch synthesis reaction water is a very complicated raw material system which primarily has the following features: the Fischer-Tropsch synthesis reaction water contains as many as 30 oxygenated volatile organic compounds including alcohols $C_1$-$C_8$, aldehydes $C_1$-$C_8$, ketones $C_1$-$C_8$, acids $C_1$-$C_8$ and esters $C_1$-$C_8$; (2) the total content of the oxygenated volatile organic compounds in the reaction water is low (only 2%-10%), except that the content of a very few components is greater than 1%, the content of most components is very low, and the content of some components is even lower than 0.1%; (3) many oxygenated volatile organic compounds, such as $C_2$+alcohol, propionaldehyde, butyraldehyde, 2-butanone, 2-pentanone, methyl acetate, propionic acid and butyric acid, may react with water to produce azeotropes; some of these oxygenated volatile organic compounds, such as methyl alcohol-acetone, methyl alcohol-2-butanone, ethyl alcohol-2-butanone, isopropanol-2-butanone, n-propyl alcohol-2-butanone, methyl acetate-methyl alcohol, methyl acetate-ethyl alcohol, methyl acetate-acetone, ethyl acetate-methyl alcohol, ethyl acetate-ethyl alcohol, ethyl acetate-isopropanol and ethyl acetate-2-butanone, may react with each other to produce azeotropes; and even some of these oxygenated volatile organic compounds, such as butanone-ethyl alcohol-water and ethyl acetate-ethyl alcohol-water, may react to produce ternary azeotropes; (4) instability: aldehyde compounds, such as acetaldehyde, propionaldehyde and butyraldehyde, in the reaction water are active and may deteriorate due to self-polymerization and oxidization; and (5) there are too many components with approximate boiling points, such as propionaldehyde (48° C.)-acetone (56.29° C.)-methyl acetate (56.94° C.), ethyl acetate (77.06° C.)-ethyl alcohol (78.29° C.)-butanone (79.64° C.), n-propyl alcohol (97.2° C.)-2-butanone (99.55° C.)-2-pentanone (102.31° C.). All these composition features determine that the Fischer-Tropsch synthesis reaction water system is very complicated, and it will be extremely difficult to separate qualified products out of the Fischer-Tropsch synthesis reaction water system.

Chinese Patents Publication No. CN101492332A, CN101555194A and CN101492360A disclose a separation method for Fischer-Tropsch synthesis reaction water, wherein Fischer-Tropsch synthesis reaction water is sequentially treated in side-extraction units including a common distillation tower, an acetic acid cutting tower, an ethyl alcohol cutting tower, an extractive distillation tower, an extractant recovery tower, an ethyl alcohol removal tower, an azeotropic distillation tower and a solvent recovery tower to separate out acetone, methyl alcohol, ethyl alcohol, n-propyl alcohol, acetic acid and other products. Chinese Patent Publication No. CN102442882A discloses a method for separating oxygenated volatile organic compounds by Fischer-Tropsch synthesis, wherein twelve towers including a mixed acid cutting tower, an acetaldehyde distillation tower, a methyl alcohol/ethyl alcohol separation tower, a methyl alcohol extractive distillation tower, a methyl alcohol distillation tower, an acetaldehyde removal tower, an ethyl alcohol tower, a propyl alcohol concentration tower, a propyl alcohol batch-azeotropic distillation tower, a carboxylic acid extraction tower, a carboxylic acid batch-distillation tower and an extractant recovery tower are used to separate acetaldehyde, acetone, methyl alcohol, ethyl alcohol, n-propyl alcohol, n-butyl alcohol, acetic acid, propionic acid, butyric acid, butanone and other products from Fischer-Tropsch synthesis reaction water.

All these separation methods directly separate the Fischer-Tropsch synthesis water by means of tower equipment, and the products separated out inevitably contain many impurities due to the large number of components in the reaction water and the complicated azeotropic components.

Chinese Patents Publication No. CN102060660A and CN103044217A disclose a method for separating and recycling oxygenated volatile organic compounds in Fischer-Tropsch synthesis reaction water, wherein Fischer-Tropsch synthesis water is treated through eleven distillation towers, including an acid separation tower, a ketone-alcohol cutting tower, an acetaldehyde tower, a propionaldehyde-acetone separation tower, an acetone tower, a propionaldehyde tower, a fusel dehydration tower, a solvent recovery tower, an aldehyde-ketone hydrogenation reduction tower, an ethyl alcohol tower and an n-propyl alcohol tower, as well as an aldehyde-ketone hydrorefining reactor to separate acetaldehyde, propionaldehyde, acetone, ethyl alcohol, n-propyl alcohol and other products out of the Fischer-Tropsch synthesis water. According to this method, the hydrorefining reactor is configured to convert aldehyde ketone impurities in mixed alcohols in fusel into alcohols by hydrogenation, but the alcohol products still cannot meet the standard due to the existence of alcohols with approximate boiling points and a small amount of non-hydrogenated aldehyde-ketone impurities, and the purity and impurity content of the aldehyde-ketone products cannot meet standard requirements either.

BRIEF SUMMARY OF THE INVENTION

The objective of the invention is to overcome the defects of the prior art by providing a method for treating oxygenated volatile organic compounds in Fischer-Tropsch synthesis reaction water, which solves the technical problem of large impurity content of products separated out in the prior art.

The objective of the invention can be fulfilled through the following technical solution:

A method for treating oxygenated volatile organic compounds in Fischer-Tropsch synthesis reaction water comprises:

(a) Enabling a Fischer-Tropsch synthesis reaction water flow to enter a concentration tower, so that a Fischer-Tropsch synthesis water flow with a water content less than 30 wt % is obtained at the top of the tower, and an acid-containing water flow is obtained at the bottom of the tower;

(b) Enabling the Fischer-Tropsch synthesis water flow with the water content less than 30 wt % to enter a hydrogenation reactor to convert all aldehyde-ketone-acid-ester carbonyl compounds in the flow into alcohols by hydrogenation, so that a mixed-alcohol water solution flow is obtained;

(c) Enabling the mixed-alcohol water solution flow to enter a carbonyl compound cutting tower to separate carbonyl compounds that are not completely reacted from the alcohols, so that an aldehyde-ketone-ester-rich flow is obtained at the top of the tower and is returned into the hydrogenation reactor for cyclic hydrogenation, and a mixed-alcohol water flow is obtained at the bottom of the tower;

(d) Enabling the mixed-alcohol water flow to enter a mixed-alcohol dehydration tower, condensing a tower top steam flow, then enabling the condensed tower top steam flow to enter a liquid-liquid separator, returning an upper oil-phase flow into the mixed-alcohol dehydration tower for circulation, extracting a lower water-phase flow, and extracting an anhydrous mixed alcohol flow from the bottom of the tower;

(e) Enabling the lower water-phase flow to enter a solvent recovery tower, so that a regenerative entrainer flow is obtained at the top of the tower and returns into the mixed-alcohol dehydration tower, and a waste water flow is extracted from the bottom of the tower and is discharged;

(f) Enabling the anhydrous mixed alcohol flow to enter an ethyl alcohol tower, so that a crude ethyl alcohol product flow is obtained at the top of the tower, and a $C_3$+mixed alcohol flow is obtained at the bottom of the tower;

(g) Enabling the crude ethyl alcohol product flow to enter an ethyl alcohol refining tower, so that a methyl alcohol-rich flow is obtained at the top of the tower, and an ethyl alcohol product flow is obtained at the bottom of the tower;

(h) Enabling the $C_3$+mixed alcohol flow to enter an isopropanol tower, so that an isopropanol product flow is obtained at the top of the tower, and a second $C_3$+mixed alcohol flow is obtained at the bottom of the tower;

(i) Enabling the second $C_3$+mixed alcohol flow to enter a propyl alcohol removal tower, so that an n-propyl alcohol and 2-butanol mixture flow is extracted from the top of the tower, and a $C_4$+mixed alcohol flow is obtained at the bottom of the tower;

(j) Enabling the n-propyl alcohol and 2-butanol mixture flow to enter an n-propyl alcohol tower to reversely make contact with an extractant flow entering the tower from the top, so that an n-propyl alcohol flow is extracted from the top of the tower, and an extractant and 2-butanol mixture flow is extracted from the bottom of the tower; and (k) Enabling the extractant and 2-butanol mixture flow to enter a 2-butanol tower, so that a 2-butanol product flow is obtained at the top of the tower, and a regenerative extractant flow is obtained at the bottom of the tower and is returned into the n-propyl alcohol tower for circulation.

A hydrogenation catalyst adopted by the hydrogenation reactor includes Zn, Cu, Al, Mg and Fe, wherein the mass ratio of Zn, Cu, Al, Mg and Fe is 10-55:15-60:0.1-10:0-1:0-1.

The Fischer-Tropsch synthesis water flow with the water content less than 30 wt % is a $C_1$-$C_8$ alcohol-aldehyde-ketone-acid-ester mixture water solution; in the hydrogenation reactor, the primarily-concentrated Fischer-Tropsch synthesis reaction water flow is hydrogenated to convert all aldehyde-ketone-acid-ester carbonyl compounds into alcohols, and all oxygenated volatile organic compounds in the reaction water are recycled in the form of alcohols, so that the components of separated raw material are simplified, and the separation difficulty is lowered. The hydrogenation product flow enters the carbonyl compound cutting tower to remove unreacted aldehydes, ketones and esters from the top of the tower and then circulates back into the hydrogenation reactor, so that the conversion rate of the aldehydes, ketones and esters are maximized, and it is guaranteed that the indicators of finally obtained alcohol products will not be compromised by aldehyde-ketone-ester impurities in hydrogenation products. Although the configuration of the hydrogenation reactor has already been disclosed in the prior art, removal of carbonyl compounds and circulation of the hydrogenation products are not performed, products obtained by a single hydrogenation process still contain a small quantity of aldehyde-ketone-ester impurities, and the indicators of final alcohol products are compromised.

The hydrogenation reactor is a multi-filled fixed bed reactor; and before entering the reactor, a mixed flow of the Fischer-Tropsch synthesis water flow and hydrogen is preheated to 190-220° C., a reaction product is condensed to 20-50° C., and an oxygenated volatile organic compound water solution is separated from the hydrogen.

The hydrogenation reactor has a hydrogenation reaction temperature of 200-250° C., a pressure of 1-5 MPa, a liquid space velocity of 0.2-3 $h^{-1}$, and a hydrogen-carbonyl ratio of 5-30.

The mixed-alcohol dehydration tower is an azeotropic distillation tower and adopts an entrainer which is one or a mixture of several of benzene, methylbenzene, cyclohexane, n-hexane and ethyl acetate.

Furthermore, the entrainer is benzene.

The ethyl alcohol tower is a vacuum distillation tower.

The n-propyl alcohol tower is an extractive distillation tower and adopts an extractant which is one or a mixture of several of ethylene glycol, 1,3-propylene glycol, and 1,2-propylene glycol.

Furthermore, the extractant is ethylene glycol.

The number of theoretical plates of the concentration tower is 20-50, the feed location is the 5th-45th plate from the top, the reflux ratio is 1-10, the tower top pressure is controlled to a normal pressure, the tower top temperature is 70-100° C., and the tower kettle temperature is 80-160° C.

The number of theoretical plates of the carbonyl compound cutting tower is 20-100, the reflux ratio is 2-10, the feed location is the 5th-90th plate from the top, the tower top pressure is controlled to a normal pressure, the tower top temperature is 65-90° C., and the tower bottom temperature is 85-110° C.

The number of theoretical plates of the mixed alcohol hydration tower is 15-60, the feed location is the 5th-50th plate from the top, the tower top pressure is controlled to a normal pressure, the tower top temperature is 50-90° C., and the tower kettle temperature is 80-120° C.

The number of theoretical plates of the solvent recovery tower is 10-60, the feed location is the 3rd-50th plate from the top, the reflux ratio is 0.5-8, the tower top pressure is controlled to a normal pressure, the tower top temperature is 45° C.-90° C., and the tower kettle temperature is 90° C.-125° C.

The number of theoretical plates of the ethyl alcohol tower is 30-150, the reflux ratio is 3-15, the feed location is the 10th-130th plate from the top, the tower top pressure is controlled to −0.5-0.9 bar by a pressure reduction operation, the tower top temperature is 30° C.-70° C., and the tower bottom temperature is 55° C.-110° C.

The number of theoretical plates of the ethyl alcohol refining tower is 20-150, the reflux ratio is 3-15, the feed location is the 10th-130th plate from the top, the top pressure of the refining tower is controlled to a normal temperature, the tower top temperature is 60-100° C., and the tower bottom temperature is 80° C.-110° C.

The number of theoretical plates of the isopropanol tower is 20-100, the reflux ratio is 1-15, the feed location is the 10th-80th plate from the top, the tower top pressure is controlled to a normal pressure, the tower top temperature is 80-105° C., and the tower bottom temperature is 110° C.-130° C.

The number of theoretical plates of the propyl alcohol tower is 20-80, the reflux ratio is 1-10, the feed location is the 10th-70th plate, the top pressure of the propyl alcohol tower is controlled to a normal temperature, the tower top temperature is 100-120° C., and the tower bottom temperature is 140° C.-160° C.

The number of theoretical plates of the propyl alcohol tower is 20-80, the reflux ratio is 1-10, the feed location of a solvent is the 2nd-10th plate, the feed location of the n-propyl alcohol and 2-butanol mixture flow is the 10th-70th plate, the feed mass ratio of the solvent and the mixture flow is 1-10, the top pressure of the propyl alcohol tower is controlled to −0.09-0.05 MPaG, the tower top temperature is 60-80° C., and the tower bottom temperature is 140° C.-170° C.

The number of theoretical plates of the 2-butanol tower is 20-80, the reflux ratio is 1-10, the feed location is the 10th-70th plate, the tower top operation pressure is controlled to −0.09-0.05 MPaG, the tower top temperature is 50-80° C., and the tower bottom temperature is 140-175° C.

Compared with the prior art, the technical solution disclosed by the invention directly perform hydrotreatment on primarily-concentrated Fischer-Tropsch synthesis reaction water to convert aldehyde-ketone-acid-ester carbonyl compounds in the flow into alcohols, all oxygenated volatile organic compounds in the reaction water are recycled in the form of alcohols, so that the components of separated raw materials are simplified, and the separation difficulty is lowered. The problem that products cannot reach the standard due to azeotropy of different oxygenated volatile organic compounds is eliminated. Compared with the prior art, the technique can convert all carbonyl compounds in an alcohol-aldehyde-ketone-acid-ester water solution into alcohols, thus having the advantages of simple separation process and high product purity.

BRIEF DESCRIPTION OF THE SEVERAL VIEWS OF THE DRAWINGS

In the FIGURES: T1, concentration tower; T2, carbonyl compound cutting tower; T3, mixed-alcohol dehydration tower; T4, solvent recovery tower; T5, ethyl alcohol tower; T6, ethyl alcohol refining tower; T7, isopropanol tower; T8, propyl alcohol removal tower; T9, n-propyl alcohol tower; T10, 2-butanol tower; R, hydrogenation reactor; F, liquid-liquid separator; 1, Fischer-Tropsch synthesis reaction water flow; 2, Fischer-Tropsch synthesis water flow with a water content less than 30 wt %; 3, acid-containing water flow; 4, mixed-alcohol water solution flow; 5, aldehyde-ketone-ester-rich flow; 6, mixed alcohol water flow; 7, tower top steam flow; 8, upper oil-phase flow; 9, lower water-phase flow; 10, anhydrous mixed alcohol flow; 11, regenerative entrainer flow; 12, waste water flow; 13, crude ethyl alcohol product flow; 14, $C_3$+mixed alcohol flow; 15, methyl alcohol-rich flow; 16, ethyl alcohol product flow; 17, isopropanol product flow; 18, second $C_3$+mixed alcohol flow; 19, n-propyl alcohol and 2-butanol mixture flow; 20, $C_4$+mixed alcohol flow; 21, n-propyl alcohol flow; 22, extractant and 2-butanol mixture flow; 23, 2-butanol mixture flow; 24, regenerative extractant flow.

DETAILED DESCRIPTION OF THE INVENTION

The invention is expounded below in combination with specific embodiments. The following embodiments will assist those skilled in the art in further understanding the invention, but are not intended to limit the invention in any forms. It should be noted that those ordinarily skilled in the art can make various transformations and improvements without deviating from the concept of the invention, and all these transformations and improvements should also fall within the protection scope of the invention.

A method for treating oxygenated volatile organic compounds in Fischer-Tropsch synthesis reaction water comprises the following steps:

(a) A Fischer-Tropsch synthesis reaction water flow enters a concentration tower, wherein the number of theoretical plates of the concentration tower is 20-50, the feed location is the 5th-45th plate from the top, the reflux ratio is 1-10, the tower top pressure is controlled to a normal pressure, the tower top temperature is 70-100° C., and the tower kettle temperature is 80-160° C.; a Fischer-Tropsch synthesis water flow with a water content less than 30 wt % is obtained at the top of the tower, and an acid-containing flow is obtained at the bottom of the tower, (b) The Fischer-Tropsch synthesis water flow with the water content less than 30 wt % enters a hydrogenation reactor, wherein a multi-filled fixed bed reactor is adopted, a hydrogenation catalyst including Zn, Cu, Al, Mg and Fe is used, and the mass ratio of Zn, Cu, Al, Mg and Fe is 10-55:15-60:0.1-10:0-1:0-1; the primarily-concentrated Fischer-Tropsch synthesis reaction water flow is directly hydrogenated in the hydrogenation reactor to convert all aldehyde-ketone-acid-ester carbonyl compounds in the flow into alcohols, and all oxygenated volatile organic compounds in the reaction water are recycled in the form of alcohols, so that the components of separated raw materials are simplified, and the separation difficulty is lowered; before entering the reactor, a mixed flow of the Fischer-Tropsch synthesis water flow and hydrogen is preheated to 190-220° C., wherein the hydrogenation reaction temperature is 200-250° C., the pressure is 1-5 MPa, the liquid space velocity is 0.2-3 $h^{-1}$, and the hydrogen-carbonyl ratio is 5-30; and after the reaction, a reaction product is condensed to 20-50° C., an oxygenated volatile organic compound water solution is separated from the hydrogen; and after the reaction;

(c) The mixed-alcohol water solution flow enters a carbonyl compound cutting tower to separate carbonyl compounds that are not completely reacted from the alcohols, wherein the number of theoretical plates of the carbonyl compound cutting tower is 20-100, the reflux ratio is 2-10, the feed location is the 5th-90th plate from the top, the tower top pressure is controlled to a normal pressure, the tower top temperature is 65-90° C., and the tower bottom temperature is 85-110° C.; an aldehyde-ketone-ester-rich flow is obtained at the top of the tower and is returned into the hydrogenation reactor for cyclic hydrogenation; and a mixed-alcohol water flow is obtained at the bottom of the tower;

(d) The mixed-alcohol water flow enters a mixed-alcohol dehydration tower, wherein the mixed-alcohol dehydration tower is an azeotropic distillation tower and adopts an entrainer which is one or a mixture of several of benzene, methylbenzene, cyclohexane, n-hexane and ethyl acetate, the number of theoretical plates of the mixed alcohol hydration tower is 15-60, the feed location is the 5th-50th plate from the top, the tower top pressure is controlled to a normal pressure, the tower top temperature is 50-90° C., and the tower kettle temperature is 80-120° C.; and a tower top steam flow is condensed and then enters a liquid-liquid separator, an upper oil-phase flow returns into the mixed-alcohol dehydration tower for circulation, a lower water-phase flow is extracted, and an anhydrous mixed alcohol flow is extracted from the bottom of the tower;

(e) The lower water-phase flow enters a solvent recovery tower, wherein the number of theoretical plates of the solvent recovery tower is 10-60, the feed location is the 3rd-50th plate from the top, the reflux ratio is 0.5-8, the tower top pressure is controlled to a normal pressure, the tower top temperature is 45° C.-90° C., and the tower kettle temperature is 90° C.-125° C.; a regenerative entrainer flow is obtained at the top of the tower and returns into the mixed-alcohol dehydration tower; and a waste water flow extracted from the bottom of the tower is discharged;

(f) The anhydrous mixed alcohol flow enters an ethyl alcohol tower, wherein the ethyl alcohol tower is a vacuum distillation tower, the number of theoretical plates of the ethyl alcohol tower is 30-150, the reflux ratio is 3-15, the feed location is the 10th-130th plate from the top, the tower top pressure is controlled to −0.5~−0.9 bar by a pressure reduction operation, the tower top temperature is 30° C.-70° C., and the tower bottom temperature is 55° C.-110° C.; a crude ethyl alcohol product flow is obtained at the top of the tower; and a $C_3$+mixed alcohol flow is obtained at the bottom of the tower;

(g) The crude ethyl alcohol product flow enters an ethyl alcohol refining tower, wherein the number of theoretical plates of the ethyl alcohol refining tower is 20-150, the reflux ratio is 3-15, the feed location is the 10th-130th plate from the top, the top pressure of the ethyl alcohol refining tower is controlled to a normal temperature, the tower top temperature is 60-100° C., and the tower bottom temperature is 80° C.-110° C.; a methyl alcohol-rich flow is obtained at the top of the tower; and an ethyl alcohol product flow is obtained at the bottom of the tower;

(h) The $C_3$+mixed alcohol flow to enter an isopropanol tower, the number of theoretical plates of the isopropanol tower is 20-100, the reflux ratio is 1-15, the feed location is the 10th-80th plate from the top, the tower top pressure is controlled to a normal temperature, the tower top temperature is 80-105° C., and the tower bottom temperature is 110° C.-130° C.; an isopropanol product flow is obtained at the top of the tower; and a second $C_3$+mixed alcohol flow is obtained at the bottom of the tower;

(i) The second $C_3$+mixed alcohol flow enters a propyl alcohol removal tower, wherein the number of theoretical plates of the propyl alcohol tower is 20-80, the reflux ratio is 1-10, the feed location is the $10^{th}$-$70^{th}$ plate, the top pressure of the propyl alcohol removal tower is controlled to a normal temperature, the tower top temperature is 100-120° C., and the tower bottom temperature is 140° C.-160° C.; an n-propyl alcohol and 2-butanol mixture flow is extracted from the top of the tower; and a $C_4$+mixed alcohol flow is obtained at the bottom of the tower;

(j) The n-propyl alcohol and 2-butanol mixture flow enters an n-propyl alcohol tower, wherein the ethyl alcohol tower is a extractive distillation tower and adopts an extractant which is one or a mixture of several of ethylene glycol, 1,3-propylene glycol, and 1,2-propylene glycol, the number of theoretical plates of the propyl alcohol tower is 20-80, the reflux ratio is 1-10, the feed location of a solvent is the 2nd-10th plate, the feed location of the n-propyl alcohol and 2-butanol mixture flow is the 10th-70th plate, the feed mass ratio of the solvent and the mixture flow is 1-10, the top pressure of the n-propyl alcohol tower is controlled to −0.09-0.05 MPaG, the tower top temperature is 60-80° C., and the tower bottom temperature is 140° C.-170° C.; and after the n-propyl alcohol and 2-butanol mixture flow reversely makes contact with an extractant flow entering the tower from the top, an n-propyl alcohol flow is extracted from the top of the tower, and g an extractant and 2-butanol mixture flow is extracted from the bottom of the tower; and (k) The extractant and 2-butanol mixture flow enters a 2-butanol tower, wherein the number of theoretical plates of the 2-butanol tower is 20-80, the reflux ratio is 1-10, the feed location is the 10th-70th plate, the tower top operation pressure is controlled to −0.09-0.05 MPaG the tower top temperature is 50-80° C., and the tower bottom temperature is 140-175° C.; a 2-butanol product flow is obtained at the top of the tower; and a regenerative extractant flow is obtained at the bottom of the tower and is returned into the n-propyl alcohol tower for circulation.

More detailed embodiments of the invention are given below to further explain the technical solutions and technical effects of the invention.

Embodiment 1

A method for treating oxygenated volatile organic compounds in Fischer-Tropsch synthesis reaction water is primarily used to solve the technical problem of large impurity content of separated products in the prior art. According to the process shown in FIG. 1, a Fischer-Tropsch synthesis reaction water flow 1 (see Table 1 for the components) entered a concentration tower T1; under the condition where the number of theoretical plates of the concentration tower T1 was 35, the reflux ratio was 6 and the feed location was the 15th plate from the top, the tower top operation pressure was controlled to 0.05 MPaG, the tower top temperature was controlled to 80-81° C., and the tower kettle temperature was controlled to 120-121° C.; a Fischer-Tropsch synthesis water flow with a water content less than 30 wt % 2 was extracted from the top of the tower, wherein the water content was 28% in this embodiment; and an acid-containing water flow 3 was extracted from the bottom of the tower. The Fischer-Tropsch synthesis water flow with the water content less than 30 wt % 2 was preheated together with hydrogen and then entered a fixed bed hydrogenation reactor R filled with a catalyst by three sections, wherein in this embodiment, the mass ratio of all components of the catalyst met Zn:Cu:Al:Mg:Fe=22:39:1.6:0.02:0.03. Under the reaction condition where the reaction temperature was 220° C., the pressure was 2.5 MPa, the liquid space velocity was 0.5 $h^{-1}$, and the molar ratio of hydrogen and carbonyl was 20, all aldehyde-ketone-acid-ester carbonyl compounds in the Fischer-Tropsch synthesis water flow with the water content less than 30 wt % 2 were converted into alcohols, so that a mixed-alcohol water solution flow 4 was obtained. The mixed-alcohol water solution flow 4 entered a carbonyl compound cutting tower T2; under the condition where the number of theoretical plates of the carbonyl compound cutting tower T2 was 60, the reflux ratio was 5 and the feed location was the 30th plate from the top, the tower top pressure was controlled to 0.05 MPaG, the tower top temperature was controlled to 83-84° C., and the tower bottom temperature was controlled to 97-98° C.; an aldehyde-ketone-ester-rich flow 5 was obtained at the top of the tower and was returned into the hydrogenation reactor R for cyclic hydrogenation; and a mixed-alcohol water flow 6 was obtained at the bottom of the tower. The mixed-alcohol water flow 6 entered a mixed-alcohol dehydration tower T3 which was an azeotropic distillation tower and adopted benzene as an entrainer; under the condition where the number of theoretical plates of the mixed-alcohol dehydration tower T3 was 30 and the feed location was the 15th plate from the top, the tower top operation pressure was controlled to 0.05 MPaG, the tower top temperature was controlled to 71.5-72.5° C., and the tower bottom temperature was controlled to 97-98° C.; a tower top steam flow 7 was condensed and then entered a liquid-liquid separator F, an upper oil-phase flow 8 flowed back; a lower water-phase was extracted as a lower water-phase flow 9; and an anhydrous mixed alcohol flow 10 was obtained at the bottom of the tower. The lower water-phase flow 9 entered a solvent recovery tower T4; under the condition where the number of theoretical plates of the solvent recovery tower T4 was 30, the reflux ratio was 1 and the feed location was the 15th plate from the top, the tower top operation pressure was controlled to 0.05 MPaG, the tower top temperature was controlled to 76-77° C., and the tower bottom temperature was controlled to 117-118° C.; and a regenerative solvent flow 11 was obtained at the top of the tower; and a waste water flow 12 was obtained at the bottom of the tower. The anhydrous mixed alcohol flow 10 entered an ethyl alcohol tower T5; under the condition where the number of theoretical plates of the ethyl alcohol tower T5 was 130, the feed location was the 65th plate from the top and the reflux ratio was 7, the tower top operation pressure was controlled to −0.07 MPaG, the tower top temperature was controlled to 50.6° C., and the tower bottom temperature was controlled to 73.8° C.; a crude ethyl alcohol product flow 13 was obtained at the top of the tower; and a $C_3$+mixed alcohol flow 14 was obtained at the bottom of the tower. The crude ethyl alcohol product flow 13 entered an ethyl alcohol refining tower T6; under the condition where the number of theoretical plates of the ethyl alcohol refining tower T6 was 120, the feed location was the 60th plate from the top and the reflux ratio was 15, the tower top pressure was controlled to 0.05 MPaG, the tower top temperature was controlled to 84-85° C., and the tower bottom temperature was controlled to 93-94° C.; a methyl alcohol-rich flow 15 was obtained at the top of the tower; and an ethyl alcohol product flow 16 was obtained at the bottom of the tower. The $C_3$+mixed alcohol flow 14 entered an isopropanol tower T7; under the condition where the number of theoretical plates of the isopropanol tower T7 was 50, the reflux ratio was 4 and the feed location was the 15th plate from the top, the tower top operation pressure was controlled to 0.05 MPaG, the tower top temperature was controlled to 92-93° C., and the tower bottom temperature was controlled to 121-122° C.; an isopropanol product flow 17 was obtained at the top of the tower; and a second $C_3$+mixed alcohol flow 18 was obtained at the bottom of the tower. The second $C_3$+mixed alcohol flow 18 entered a propyl alcohol removal tower T8; under the condition where the number of theoretical plates of the propyl alcohol removal tower T8 was 50, the reflux ratio was 5 and the feed location was the 25th plate from the top, the tower top operation pressure was controlled to 0.05 MPaG, the tower top temperature was controlled to 109° C., and the tower bottom temperature was controlled to 153-154° C.; an n-propyl alcohol and 2-butanol mixture flow 19 was obtained at the top of the tower; and a $C_4$+mixed alcohol flow 20 was obtained at the bottom of the tower. The n-propyl alcohol and 2-butanol mixture flow 19 entered an n-propyl alcohol tower T9; under the condition where ethylene glycol was used as an extractant, the number of theoretical plates of the n-propyl alcohol tower T9 was 45, the reflux ratio was 5, the feed location of the mixture flow was the 22nd plate from the top, the feed location of the extractant was the 4th plate from the top and the feed mass ratio of the extractant and the mixture was 3.3, the operation pressure was controlled to −0.07 MPaG, the tower top temperature was controlled to 69-70° C., and the tower bottom temperature was controlled to 160-161° C.; an n-propyl alcohol flow 21 with a water content less than 30 wt % was obtained at the top of the tower; and an extractant and 2-butanol mixture flow 22 with a water content less than 30 wt % was obtained at the bottom of the tower. The extractant and 2-butanol mixture flow with the water content less than 30 wt % 22 entered a 2-butanol tower T10; under the condition where the number of theoretical plates of the 2-butanol tower T10 was 45, the feed location was the 22nd plate from the top and the reflux ratio was 5, the tower top operation pressure was controlled to −0.08 MPaG, the tower top temperature was controlled to 62-63° C., and the tower bottom temperature was controlled to 159-160° C.; a 2-butanol product flow 23 was obtained at the top of the tower; and a regenerative extractant flow with a water content less than 30 wt % 24 was obtained at the bottom of the tower and was returned into the n-propyl alcohol tower T9 for circulation. Flow data obtained by separation under the aforesaid conditions is shown in Table 1. The indicators of products are shown in Table 2.

TABLE 1

Flow data of all towers in Embodiment 1

| Flow | Water | Total aldehyde | Total ketone | Total acid | Total ester | Total alcohol | Ethyl alcohol | Isopropanol | n-propyl alcohol | 2-butanol |
|---|---|---|---|---|---|---|---|---|---|---|
| 1 | 93.91 | 0.68 | 1.18 | 0.63 | 0.01 | 3.59 | 2.31 | 0.16 | 0.58 | 0.00 |
| 2 | 28.22 | 8.86 | 15.38 | 0.00 | 0.20 | 47.35 | 30.62 | 2.08 | 7.69 | 0.00 |
| 3 | 99.27 | 0.01 | 0.03 | 0.68 | 0.00 | 0.01 | 0.00 | 0.00 | 0.00 | 0.00 |
| 4 | 25.22 | 0.32 | 1.34 | 0.00 | 0.16 | 72.96 | 42.23 | 15.01 | 7.14 | 2.06 |
| 5 | 6.76 | 2.43 | 10.33 | 0.00 | 1.20 | 79.28 | 64.30 | 12.10 | 0.00 | 0.00 |
| 6 | 27.96 | 0.01 | 0.00 | 0.00 | 0.01 | 72.02 | 38.95 | 15.44 | 8.21 | 2.37 |
| 7 | 7.38 | 0.00 | 0.00 | 0.00 | 0.00 | 23.01 | 8.77 | 1.58 | 0.14 | 0.00 |
| 8 | 0.27 | 0.00 | 0.00 | 0.00 | 0.00 | 7.29 | 3.05 | 0.83 | 0.07 | 0.00 |
| 9 | 26.30 | 0.00 | 0.00 | 0.00 | 0.00 | 64.80 | 23.94 | 3.58 | 0.34 | 0.01 |
| 10 | 0.15 | 0.01 | 0.00 | 0.00 | 0.01 | 99.68 | 53.87 | 21.36 | 11.35 | 3.28 |
| 11 | 4.56 | 0.00 | 0.00 | 0.00 | 0.00 | 83.91 | 31.00 | 4.64 | 0.44 | 0.01 |
| 12 | 100.00 | 0.00 | 0.00 | 0.00 | 0.00 | 0.00 | 0.00 | 0.00 | 0.00 | 0.00 |
| 13 | 0.28 | 0.02 | 0.00 | 0.00 | 0.02 | 99.41 | 97.88 | 0.04 | 0.00 | 0.00 |
| 14 | 0.00 | 0.00 | 0.00 | 0.00 | 0.00 | 100.00 | 0.10 | 47.41 | 25.23 | 7.28 |
| 15 | 1.03 | 0.16 | 0.02 | 0.00 | 0.27 | 95.41 | 78.85 | 0.00 | 0.00 | 0.00 |
| 16 | 0.21 | 0.00 | 0.00 | 0.00 | 0.00 | 99.79 | 99.67 | 0.04 | 0.00 | 0.00 |
| 17 | 0.00 | 0.00 | 0.00 | 0.00 | 0.00 | 100.00 | 0.21 | 99.78 | 0.01 | 0.00 |
| 18 | 0.00 | 0.00 | 0.00 | 0.00 | 0.00 | 100.00 | 0.00 | 0.01 | 48.06 | 13.87 |
| 19 | 0.00 | 0.00 | 0.00 | 0.00 | 0.00 | 100.00 | 0.00 | 0.02 | 77.65 | 22.33 |
| 20 | 0.00 | 0.00 | 0.00 | 0.00 | 0.00 | 100.00 | 0.00 | 0.00 | 0.01 | 0.12 |
| 21 | 0.00 | 0.00 | 0.00 | 0.00 | 0.00 | 100.00 | 0.00 | 0.02 | 99.86 | 0.12 |
| 22 | 0.00 | 0.00 | 0.00 | 0.00 | 0.00 | 6.19 | 0.00 | 0.01 | 6.18 |  |
| 23 | 0.00 | 0.00 | 0.00 | 0.00 | 0.00 | 100.00 | 0.00 | 0.00 | 0.16 | 99.83 |
| 24 | 0.00 | 0.00 | 0.00 | 0.00 | 0.00 | 0.01 | 0.00 | 0.00 | 0.00 | 0.01 |

TABLE 2

Indictors of all products in Embodiment 1

| Components | Ethyl alcohol | Isopropanol | n-propyl alcohol | 2-butanol |
|---|---|---|---|---|
| Water | 0.208 |  |  |  |
| Butyraldehyde | 0.003 |  |  |  |
| Methyl alcohol | 0.080 |  |  |  |
| 2-butanone | 0.001 |  |  |  |
| Isopropanol | 0.041 | 99.782 | 0.021 |  |
| Ethyl alcohol | 99.667 | 0.210 | 0.000 |  |
| 2-butanol |  | 0.002 | 0.121 | 99.828 |
| n-propyl alcohol |  | 0.006 | 99.856 | 0.162 |
| Isobutanol |  |  | 0.000 | 0.010 |
| Ethylene glycol |  |  |  | 0.001 |

Embodiment 2

Figure 1:
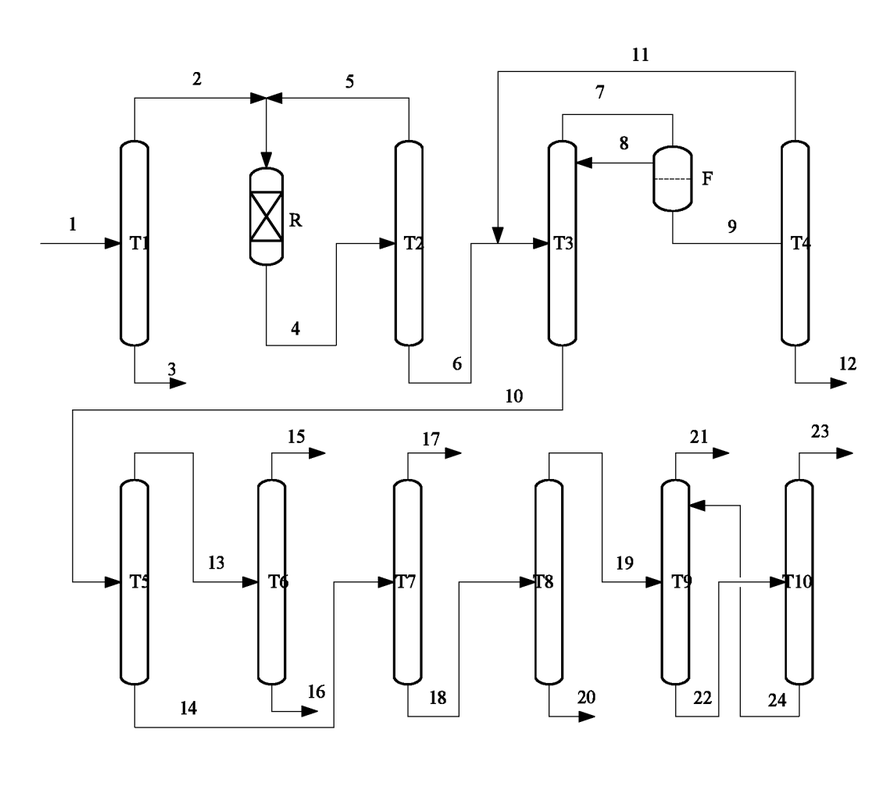
FIG. 1 is a process flow diagram of an embodiment of the invention.

According to a method for treating oxygenated volatile organic compounds in Fischer-Tropsch synthesis reaction water in this embodiment, the components of Fischer-Tropsch synthesis reaction water were not changed, and operation conditions of all units were changed. Particularly, a Fischer-Tropsch synthesis reaction water flow 1 entered a concentration tower T1; under the condition where the number of theoretical plates of the concentration tower T1 was 30, the reflux ratio was 5 and the feed location was the 9th plate from the top, the tower top operation pressure was controlled to 0.05 MPaG, the tower top temperature was controlled to 80-81° C., and the tower kettle temperature was controlled to 120-121° C.; a Fischer-Tropsch synthesis water flow with a water content less than 30 wt % 2 was extracted from the top of the tower, wherein the water content was 28% in this embodiment; and an acid-containing water flow 3 was extracted from the bottom of the tower. The Fischer-Tropsch synthesis water flow with the water content less than 30 wt % 2 was preheated together with hydrogen and then entered a fixed bed hydrogenation reactor R filled with a catalyst by three sections, wherein in this embodiment, the mass ratio of all components of the catalyst met Zn:Cu:Al:Mg:Fe=14:42:4:0.1:0.05. Under the reaction condition where the reaction temperature was 215° C., the pressure was 3 MPa, the liquid space velocity was 0.8 h$^{-1}$, and the molar ratio of hydrogen and carbonyl was 15, all aldehyde-ketone-acid-ester carbonyl compounds in the Fischer-Tropsch synthesis water flow with the water content less than 30 wt % 2 were converted into alcohols, so that a mixed-alcohol water solution flow 4 was obtained. The mixed-alcohol water solution flow 4 entered a carbonyl compound cutting tower T2; under the condition where the number of theoretical plates of the carbonyl compound cutting tower T2 was 40, the reflux ratio was 8 and the feed location was the 20th plate from the top, the tower top pressure was controlled to 0.05 MPaG, the tower top temperature was controlled to 82-83° C., and the tower bottom temperature was controlled to 97-98° C.; an aldehyde-ketone-ester-rich flow 5 was obtained at the top of the tower and was returned into the hydrogenation reactor R for cyclic hydrogenation; and a mixed-alcohol water flow 6 was obtained at the bottom of the tower. The mixed-alcohol water flow 6 entered a mixed-alcohol dehydration tower T3; under the condition where the number of theoretical plates of the mixed-alcohol dehydration tower T3 was 35 and the feed location was the 17th plate from the top, the tower top operation pressure was controlled to 0.05 MPaG, the tower top temperature was controlled to 71.5-72.5° C., and the tower bottom temperature was controlled to 97-98° C.; a tower top steam flow 7 was condensed and then entered a liquid-liquid separator F; an upper oil-phase flow 8 flowed back; a lower water-phase was extracted as a lower water-phase flow 9; and an anhydrous mixed alcohol flow 10 was obtained at the bottom of the tower. The lower water-phase flow 9 entered a solvent recovery tower T4; under the condition where the number of theoretical plates of the solvent recovery tower T4 was 25, the reflux ratio was 1 and the feed location was the 12th plate from the top, the tower top operation pressure was controlled to 0.05 MPaG, the tower top temperature was controlled to 76-77° C., and the tower bottom temperature was controlled to 117-118° C.; a regenerative solvent flow 11 was obtained at the top of the tower; and a waste water flow 12 was obtained at the bottom of the tower. The anhydrous mixed alcohol flow 10 entered an ethyl alcohol tower T5; under the condition where the number of theoretical plates of the ethyl alcohol tower T5 was 100, the feed location was the 50th plate from the top and the reflux ratio was 8, the tower top operation pressure was controlled to −0.09 MPaG, the tower top temperature was controlled to 30.3-31.3° C., and the tower bottom temperature was controlled to 62.3-63.3° C.; a crude ethyl alcohol product flow 13 was obtained at the top of the tower; and a C$_3$+mixed alcohol flow 14 was obtained at the bottom of the tower. The crude ethyl alcohol product flow 13 entered an ethyl alcohol refining tower T6; under the condition where the number of theoretical plates of the ethyl alcohol refining tower T6 was 60, the feed location was the 30th plate from the top and the reflux ratio was 12, the tower top pressure was controlled to 0.05 MPaG, the tower top temperature was controlled to 84.6-85.6° C., and the tower bottom temperature was controlled to 93.3-94.3° C.; a methyl alcohol-rich flow 15 was obtained at the top of the tower; and an ethyl alcohol product flow 16 was obtained at the bottom of the tower. The C$_3$+mixed alcohol flow 14 entered an isopropanol tower T7; under the condition where the number of theoretical plates of the isopropanol tower T7 was 50, the reflux ratio was 4 and the feed location was the 20th plate from the top, the tower top operation pressure was controlled to 0.05 MPaG, the tower top temperature was controlled to 92.4-93.4° C., and the tower bottom temperature was controlled to 120.7-121.7° C.; an isopropanol product flow 17 was obtained at the top of the tower; and a second C$_3$+mixed alcohol flow 18 was obtained at the bottom of the tower. The second C$_3$+mixed alcohol flow 18 entered a propyl alcohol removal tower T8; under the condition where the number of theoretical plates of the propyl alcohol removal tower T8 was 40, the reflux ratio was 5 and the feed location was the 20th plate from the top, the tower top operation pressure was controlled to 0.05 MPaG, the tower top temperature was controlled to 109.3° C., and the tower bottom temperature was controlled to 152.5-153.5° C.; an n-propyl alcohol and 2-butanol mixture flow 19 was obtained at the top of the tower; and a C$_4$+mixed alcohol flow 20 was obtained at the bottom of the tower. The n-propyl alcohol and 2-butanol mixture flow 19 entered an n-propyl alcohol tower T9; under the condition where 1,3-propylene glycol was used as an extractant, the number of theoretical plates of the n-propyl alcohol tower T9 was 50, the reflux ratio was 3, the feed location of the mixture flow was the 25nd plate from the top, the feed location of the extractant was the 4th plate from the top and the feed mass ratio of the extractant and the mixture flow was 3.3, the operation pressure was controlled to −0.07 MPaG, the tower top temperature was controlled to 60.6-61.6° C., and the tower bottom temperature was controlled to 154-155° C.; an n-propyl alcohol flow with a water content less than 30 wt % 21 was obtained at the top of the tower; and an extractant and 2-butanol mixture flow with the water content less than 30 wt % 22 was obtained at the bottom of the tower. The extractant and 2-butanol mixture flow with the water content less than 30 wt % 22 entered a 2-butanol tower T10; under the condition where the number of theoretical plates of the 2-butanol tower T10 was 50, the feed location was the 25nd plate from the top and the reflux ratio was 3, the tower top operation pressure was controlled to −0.09 MPaG, the tower top temperature was controlled to 49.8-50.8° C., and the tower bottom temperature was controlled to 161-162° C.; a 2-butanol product flow 23 was obtained at the top of the tower; and a regenerative extractant flow with a water content less than 30 wt % 24 was obtained at the bottom of the tower and was returned into the n-propyl alcohol tower T9 for circulation. Flow data obtained by separation under the aforesaid conditions was shown in Table 3. The indicators of the products were shown in Table 4.

TABLE 3

Flow data of all towers in Embodiment 2

| Flow | Water | Total aldehyde | Total ketone | Total acid | Total ester | Total alcohol | Ethyl alcohol | Isopropanol | n-propyl alcohol | 2-butanol |
|---|---|---|---|---|---|---|---|---|---|---|
| 1  | 93.91  | 0.68 | 1.18  | 0.63 | 0.01 | 3.59   | 2.31  | 0.16  | 0.58  | 0.00  |
| 2  | 28.39  | 8.91 | 15.32 | 0.00 | 0.20 | 47.17  | 30.50 | 2.07  | 7.66  | 0.00  |
| 3  | 99.27  | 0.01 | 0.03  | 0.68 | 0.00 | 0.01   | 0.00  | 0.00  | 0.00  | 0.00  |
| 4  | 24.89  | 0.32 | 1.30  | 0.00 | 0.17 | 73.33  | 42.53 | 14.48 | 6.95  | 2.00  |
| 5  | 6.58   | 2.09 | 8.62  | 0.00 | 1.10 | 81.61  | 63.47 | 9.42  | 0.05  | 0.00  |
| 6  | 28.13  | 0.01 | 0.00  | 0.00 | 0.00 | 71.86  | 38.81 | 15.38 | 8.18  | 2.36  |
| 7  | 7.46   | 0.00 | 0.00  | 0.00 | 0.00 | 22.89  | 8.82  | 1.59  | 0.15  | 0.00  |
| 8  | 0.27   | 0.00 | 0.00  | 0.00 | 0.00 | 7.25   | 3.07  | 0.84  | 0.07  | 0.00  |
| 9  | 26.65  | 0.00 | 0.00  | 0.00 | 0.00 | 64.65  | 24.18 | 3.61  | 0.35  | 0.01  |
| 10 | 0.15   | 0.01 | 0.00  | 0.00 | 0.00 | 99.70  | 53.85 | 21.34 | 11.34 | 3.27  |
| 11 | 4.62   | 0.00 | 0.00  | 0.00 | 0.00 | 84.06  | 31.44 | 4.70  | 0.45  | 0.01  |
| 12 | 100.00 | 0.00 | 0.00  | 0.00 | 0.00 | 0.00   | 0.00  | 0.00  | 0.00  | 0.00  |
| 13 | 0.27   | 0.01 | 0.00  | 0.00 | 0.00 | 99.45  | 97.84 | 0.19  | 0.00  | 0.00  |
| 14 | 0.00   | 0.00 | 0.00  | 0.00 | 0.00 | 100.00 | 0.10  | 47.18 | 25.20 | 7.27  |
| 15 | 0.76   | 0.08 | 0.01  | 0.00 | 0.03 | 97.37  | 88.32 | 0.03  | 0.00  | 0.00  |
| 16 | 0.18   | 0.00 | 0.00  | 0.00 | 0.00 | 99.82  | 99.52 | 0.22  | 0.00  | 0.00  |
| 17 | 0.00   | 0.00 | 0.00  | 0.00 | 0.00 | 100.00 | 0.21  | 99.76 | 0.02  | 0.00  |
| 18 | 0.00   | 0.00 | 0.00  | 0.00 | 0.00 | 100.00 | 0.00  | 0.01  | 47.79 | 13.80 |
| 19 | 0.00   | 0.00 | 0.00  | 0.00 | 0.00 | 100.00 | 0.00  | 0.02  | 77.61 | 22.34 |
| 20 | 0.00   | 0.00 | 0.00  | 0.00 | 0.00 | 100.00 | 0.00  | 0.00  | 0.01  | 0.10  |
| 21 | 0.00   | 0.00 | 0.00  | 0.00 | 0.00 | 100.00 | 0.00  | 0.02  | 99.85 | 0.12  |
| 22 | 0.00   | 0.00 | 0.00  | 0.00 | 0.00 | 6.20   | 0.00  | 0.00  | 0.01  | 6.18  |
| 23 | 0.00   | 0.00 | 0.00  | 0.00 | 0.00 | 100.00 | 0.00  | 0.00  | 0.16  | 99.70 |
| 24 | 0.00   | 0.00 | 0.00  | 0.00 | 0.00 | 0.01   | 0.00  | 0.00  | 0.00  | 0.01  |

TABLE 4

Indictors of all products in Embodiment 2

| Components | Ethyl alcohol | Isopropanol | n-propyl alcohol | 2-butanol |
|---|---|---|---|---|
| Water | 0.18 | | | |
| Methyl alcohol | 0.08 | | | |
| Isopropanol | 0.22 | 99.76 | 0.02 | |
| Ethyl alcohol | 99.52 | 0.21 | 0.00 | |
| 2-butanol | | | 0.12 | 99.70 |
| n-propyl alcohol | | 0.02 | 99.85 | 0.16 |
| Isobutanol | | | | 0.14 |

Embodiment 3

According to a method for treating oxygenated volatile organic compounds in Fischer-Tropsch synthesis reaction water in this embodiment, the components of Fischer-Tropsch synthesis reaction water flow were changed, and operation conditions of all towers were as set as follows. Particularly, a Fischer-Tropsch synthesis reaction water flow 1 entered a concentration tower T1; under the condition where the number of theoretical plates of the concentration tower T1 was 40, the reflux ratio was 4 and the feed location was the 17th plate from the top, the tower top operation pressure was controlled to 0.05 MPaG, the tower top temperature was controlled to 78-79° C., and the tower kettle temperature was controlled to 120-121° C.; a Fischer-Tropsch synthesis water flow with a water content less than 30 wt % 2 was extracted from the top of the tower, wherein the water content was 24% in this embodiment; and an acid-containing water flow 3 was extracted from the bottom of the tower. The Fischer-Tropsch synthesis water flow with the water content less than 30 wt % 2 was preheated together with hydrogen and then entered a fixed bed hydrogenation reactor R filled with a catalyst by three sections, wherein in this embodiment, the mass ratio of all components of the catalyst met Zn:Cu:Al:Mg:Fe=45:24:0.7:0:0.1. Under the reaction condition where the reaction temperature was 225° C., the pressure was 2 MPa, the liquid space velocity was 1 h-1, and the molar ratio of hydrogen and carbonyl was 10, all aldehyde-ketone-acid-ester carbonyl compounds in the Fischer-Tropsch synthesis water flow with the water content less than 30 wt % 2 were converted into alcohols, so that a mixed-alcohol water solution flow 4 was obtained. The mixed-alcohol water solution flow 4 entered a carbonyl compound cutting tower T2; under the condition where the number of theoretical plates of the carbonyl compound cutting tower T2 was 40, the reflux ratio was 8 and the feed location was the 20th plate from the top, the tower top pressure was controlled to 0.05 MPaG, the tower top temperature was controlled to 82.6-83.6° C., and the tower bottom temperature was controlled to 96-97° C.; an aldehyde-ketone-ester-rich flow 5 was obtained at the top of the tower and was returned into the hydrogenation reactor R for cyclic hydrogenation; and a mixed-alcohol water flow 6 was obtained at the bottom of the tower. The mixed-alcohol water flow 6 entered a mixed-alcohol dehydration tower T3 which adopted n-hexane as an entrainer; under the condition where the number of theoretical plates of the mixed-alcohol dehydration tower T3 was 40 and the feed location was the 20th plate from the top, the tower top operation pressure was controlled to 0.05 MPaG, the tower top temperature was controlled to 72-73° C., and the tower bottom temperature was controlled to 96-97° C.; a tower top steam flow 7 was condensed and then entered a liquid-liquid separator F, an upper oil-phase flow 8 flowed back; a lower water-phase was extracted as a lower water-phase flow 9; and an anhydrous mixed alcohol flow 10 was obtained at the bottom of the tower. The lower water-phase flow 9 entered a solvent recovery tower T4; under the condition where the number of theoretical plates of the solvent recovery tower T4 was 30, the reflux ratio was 1 and the feed location was the 15th plate from the top, the tower top operation pressure was controlled to 0.05 MPaG, the tower top temperature was controlled to 76-77° C., and the tower bottom temperature was controlled to 117-118° C.; a regenerative solvent flow 11 was obtained at the top of the tower; and a waste water flow 12 was obtained at the bottom of the tower. The anhydrous mixed alcohol flow 10 entered an ethyl alcohol tower T5; under the condition where the number of theoretical plates of the ethyl alcohol tower T5 was 80, the feed location was the 40th plate from the top and the reflux ratio was 8, the tower top operation pressure was controlled to −0.09 MPaG, the tower top temperature was controlled to 30.8° C., and the tower bottom temperature was controlled to 55° C.; a crude ethyl alcohol product flow 13 was obtained at the top of the tower; and a $C_3$+mixed alcohol flow 14 was obtained at the bottom of the tower. The crude ethyl alcohol product flow 13 entered an ethyl alcohol refining tower T6; under the condition where the number of theoretical plates of the ethyl alcohol refining tower T6 was 40, the feed location was the 20th plate from the top and the reflux ratio was 15, the tower top pressure was controlled to 0.05 MPaG, the tower top temperature was controlled to 84.6-85.6° C., and the tower bottom temperature was controlled to 93.3-94.3° C.; a methyl alcohol-rich flow 15 was obtained at the top of the tower; and an ethyl alcohol product flow 16 was obtained at the bottom of the tower. The $C_3$+mixed alcohol flow 14 entered an isopropanol tower T7; under the condition where the number of theoretical plates of the isopropanol tower T7 was 40, the reflux ratio was 8 and the feed location was the 20th plate from the top, the tower top operation pressure was controlled to 0.05 MPaG, the tower top temperature was controlled to 92.4-93.4° C., and the tower bottom temperature was controlled to 118-119° C.; an isopropanol product flow 17 was obtained at the top of the tower; and a second $C_3$+mixed alcohol flow 18 was obtained at the bottom of the tower. The second $C_3$+mixed alcohol flow 18 entered a propyl alcohol removal tower T8; under the condition where the number of theoretical plates of the propyl alcohol removal tower T8 was 40, the reflux ratio was 5 and the feed location was the 20th plate from the top, the tower top operation pressure was controlled to 0.05 MPaG, the tower top temperature was controlled to 108-109° C., and the tower bottom temperature was controlled to 142-143° C.; an n-propyl alcohol and 2-butanol mixture flow 19 was obtained at the top of the tower; and a $C_4$+mixed alcohol flow 20 was obtained at the bottom of the tower. The n-propyl alcohol and 2-butanol mixture flow 19 entered an n-propyl alcohol tower T9; under the condition where 1,2-propylene glycol was used as an extractant, the number of theoretical plates of the n-propyl alcohol tower T9 was 50, the reflux ratio was 2, the feed location of the mixture flow was the 25nd plate from the top, the feed location of the extractant was the 6th plate from the top and the feed mass ratio of the extractant and the mixture flow was 4, the operation pressure was controlled to −0.09 MPaG, the tower top temperature was controlled to 48-49° C., and the tower bottom temperature was controlled to 141-142° C.; an n-propyl alcohol flow with a water content less than 30 wt % 21 was obtained at the top of the tower; and an extractant and 2-butanol mixture flow with a water content less than 30 wt % 22 was obtained at the bottom of the tower. The extractant and 2-butanol mixture flow with the water content less than 30 wt % 22 entered a 2-butanol tower T10; under the condition where the number of theoretical plates of the 2-butanol tower T10 was 50, the feed location was the 25nd plate from the top and the reflux ratio was 4, the tower top operation pressure was controlled to −0.09 MPaG, the tower top temperature was controlled to 50-51° C., and the tower bottom temperature was controlled to 161-162° C.; a 2-butanol product flow 23 was obtained at the top of the tower; and a regenerative extractant flow with a water content less than 30 wt % 24 was obtained at the bottom of the tower and was returned into the n-propyl alcohol tower T9 for circulation. Flow data obtained by separation under the aforesaid conditions was shown in Table 5. The indicators of the products were shown in Table 6.

shown in FIG. 1, wherein organic components of a Fischer-Tropsch synthesis reaction water flow 1 were changed, and operation conditions of all towers were set as follows. Particularly, the Fischer-Tropsch synthesis reaction water flow 1 (see Table 1 for the components) entered a concentration tower T1; under the condition where the number of theoretical plates of the concentration tower T1 was 20, the reflux ratio was 1 and the feed location was the 5th plate from the top, the tower top operation pressure was controlled to 0.05 MPaG, the tower top temperature was controlled to 70° C., and the tower kettle temperature was controlled to 120° C.; a Fischer-Tropsch synthesis water flow with a water content less than 30 wt % 2 was extracted from the top of the tower, wherein the water content was 29% in this embodiment; and an acid-containing water flow 3 was extracted from the bottom of the tower. The Fischer-Tropsch synthesis water flow with the water content less than 30 wt % 2 was preheated together with hydrogen and then entered a fixed bed hydrogenation reactor R filled with a catalyst by three sections, wherein in this embodiment, the mass ratio of all components of the catalyst met Zn:Cu:Al:Mg:Fe=11:55:6:0.2:0.3. Under the reaction condition where the reaction temperature was 200° C., the pressure was 1 MPa, the liquid space velocity was 0.2 h-1, and the molar ratio of hydrogen and carbonyl was 5, all aldehyde-ketone-acid-ester carbonyl compounds in the Fischer-Tropsch synthesis water flow with the water content less than 30 wt % 2 were converted into alcohols, so that a mixed-alcohol water solution flow 4 was obtained. The mixed-alcohol water solution flow 4 entered a carbonyl compound cutting tower T2; under the condition where the number of theoretical plates of the carbonyl compound cutting tower T2 was 20, the reflux ratio is 2 and the feed location was the 5th plate from the top, the tower top pressure was controlled to 0.05 MPaG, the tower top temperature was controlled to 65° C., and the tower bottom temperature was controlled to 85° C.; an aldehyde-ketone-ester-rich flow 5 was obtained at the top of the tower and was returned into the hydrogenation reactor R for cyclic hydrogenation; and a mixed-alcohol water flow 6 was obtained at the bottom of the tower.

TABLE 5

Flow data of all towers in Embodiment 3

| Flow | Water | Total aldehyde | Total ketone | Total alcohol | Total acid | Total ester | Ethyl alcohol | isopropanol | n-propyl alcohol | 2-butanol |
|---|---|---|---|---|---|---|---|---|---|---|
| 1 | 92.28 | 0.97 | 1.03 | 3.84 | 1.88 | 0.01 | 2.79 | 0.08 | 0.60 | 0.00 |
| 2 | 24.22 | 12.68 | 13.43 | 49.57 | 0.00 | 0.10 | 36.50 | 1.10 | 7.91 | 0.00 |
| 3 | 97.91 | 0.00 | 0.00 | 0.06 | 2.03 | 0.00 | 0.00 | 0.00 | 0.00 | 0.00 |
| 4 | 21.73 | 0.48 | 1.21 | 76.48 | 0.00 | 0.10 | 50.76 | 11.30 | 7.67 | 1.73 |
| 5 | 5.71 | 3.75 | 9.81 | 79.97 | 0.00 | 0.77 | 70.74 | 3.81 | 0.00 | 0.00 |
| 6 | 23.98 | 0.02 | 0.00 | 76.00 | 0.00 | 0.00 | 47.96 | 12.35 | 8.75 | 1.98 |
| 7 | 6.65 | 0.00 | 0.00 | 24.01 | 0.00 | 0.00 | 10.65 | 1.17 | 0.12 | 0.00 |
| 8 | 0.30 | 0.00 | 0.00 | 8.20 | 0.00 | 0.00 | 3.98 | 0.63 | 0.06 | 0.00 |
| 9 | 23.53 | 0.00 | 0.00 | 66.04 | 0.00 | 0.00 | 28.39 | 2.60 | 0.27 | 0.00 |
| 10 | 0.11 | 0.02 | 0.00 | 99.68 | 0.00 | 0.01 | 62.90 | 16.20 | 11.48 | 2.59 |
| 11 | 4.63 | 0.00 | 0.00 | 82.36 | 0.00 | 0.00 | 35.40 | 3.24 | 0.34 | 0.00 |
| 12 | 100.00 | 0.00 | 0.00 | 0.00 | 0.00 | 0.00 | 0.00 | 0.00 | 0.00 | 0.00 |
| 13 | 0.18 | 0.04 | 0.00 | 99.51 | 0.00 | 0.01 | 98.17 | 0.08 | 0.00 | 0.00 |
| 14 | 0.00 | 0.00 | 0.00 | 100.00 | 0.00 | 0.00 | 0.10 | 44.90 | 31.91 | 7.21 |
| 15 | 0.65 | 0.32 | 0.02 | 96.18 | 0.00 | 0.09 | 84.21 | 0.00 | 0.00 | 0.00 |
| 16 | 0.13 | 0.01 | 0.00 | 99.87 | 0.00 | 0.00 | 99.70 | 0.09 | 0.00 | 0.00 |
| 17 | 0.00 | 0.00 | 0.00 | 100.00 | 0.00 | 0.00 | 0.22 | 99.75 | 0.02 | 0.00 |
| 18 | 0.00 | 0.00 | 0.00 | 100.00 | 0.00 | 0.00 | 0.00 | 0.01 | 58.00 | 13.11 |
| 19 | 0.00 | 0.00 | 0.00 | 100.00 | 0.00 | 0.00 | 0.00 | 0.01 | 81.52 | 18.40 |
| 20 | 0.00 | 0.00 | 0.00 | 100.00 | 0.00 | 0.00 | 0.00 | 0.00 | 0.01 | 0.06 |
| 21 | 0.00 | 0.00 | 0.00 | 100.00 | 0.00 | 0.00 | 0.00 | 0.02 | 99.71 | 0.20 |
| 22 | 0.00 | 0.00 | 0.00 | 5.27 | 0.00 | 0.00 | 0.00 | 0.00 | 0.01 | 5.26 |
| 23 | 0.00 | 0.00 | 0.00 | 100.00 | 0.00 | 0.00 | 0.00 | 0.00 | 0.19 | 99.76 |
| 24 | 0.00 | 0.00 | 0.00 | 0.01 | 0.00 | 0.00 | 0.00 | 0.00 | 0.00 | 0.01 |

TABLE 6

Indictors of all products in Embodiment 3

| Component | Ethyl alcohol | Isopropanol | n-propyl alcohol | 2-butanol |
|---|---|---|---|---|
| Water | 0.13 | | | |
| Butyraldehyde | 0.01 | | | |
| Methyl alcohol | 0.08 | | | |
| Isopropanol | 0.09 | 99.75 | | 0.02 |
| Ethyl alcohol | 99.70 | 0.22 | | |
| 2-butanol | | | 0.20 | 99.76 |
| n-propyl alcohol | | 0.02 | 99.71 | 0.19 |
| Isobutanol | | | 0.07 | 0.05 |

Embodiment 4

A method for treating oxygenated volatile organic compounds in Fischer-Tropsch synthesis reaction water in this embodiment was implemented according to the process The mixed-alcohol water flow 6 entered a mixed-alcohol dehydration tower T3 which adopted benzene as an entrainer; under the condition where the number of theoretical plates of the mixed-alcohol dehydration tower T3 was 15 and the feed location was the 5th plate from the top, the tower top operation pressure was controlled to 0.05 MPaG, the tower top temperature was controlled to 50° C., and the tower bottom temperature was controlled to 80° C.; a tower top steam flow 7 was condensed and then entered a liquid-liquid separator F; an upper oil-phase flow 8 flowed back; a lower water-phase was extracted as a lower water-phase flow 9; and an anhydrous mixed alcohol flow 10 was obtained at the bottom of the tower. The lower water-phase flow 9 entered a solvent recovery tower T4; under the condition where the number of theoretical plates of the solvent recovery tower T4 was 10, the reflux ratio was 0.5 and the feed location was the 5th plate from the top, the tower top operation pressure was controlled to 0.05 MPaG, the tower top temperature was controlled to 45° C., and the tower bottom temperature was controlled to 90° C.; a regenerative solvent flow 11 was obtained at the top of the tower; and a waste water flow 12 was obtained at the bottom of the tower.

The anhydrous mixed alcohol flow 10 entered an ethyl alcohol tower T5; under the condition where the number of theoretical plates of the ethyl alcohol tower T5 was 30, the feed location was the 15th plate from the top and the reflux ratio was 3, the tower top operation pressure was controlled to −0.09 MPaG, the tower top temperature was controlled to 30° C., and the tower bottom temperature was controlled to 55° C.; a crude ethyl alcohol product flow 13 was obtained at the top of the tower; and a $C_3$+mixed alcohol flow 14 was obtained at the bottom of the tower. The crude ethyl alcohol product flow 13 entered an ethyl alcohol refining tower T6; under the condition where the number of theoretical plates of the ethyl alcohol refining tower T6 was 20, the feed location was the 10th plate from the top and the reflux ratio was 1, the tower top pressure was controlled to 0.05 MPaG, the tower top temperature was controlled to 60° C., and the tower bottom temperature was controlled to 80° C.; a methyl alcohol-rich flow 15 was obtained at the top of the tower; and an ethyl alcohol product flow 16 with a purity of 99.2% was obtained at the bottom of the tower.

The $C_3$+mixed alcohol flow 14 entered an isopropanol tower T7; under the condition where the number of theoretical plates of the isopropanol tower T7 was 20, the reflux ratio was 1 and the feed location was the 10th plate from the top, the tower top operation pressure was controlled to 0.05 MPaG, the tower top temperature was controlled to 80° C., and the tower bottom temperature was controlled to 110° C.; an isopropanol product flow 17 with a purity of 99.7% was obtained at the top of the tower; and a second $C_3$+mixed alcohol flow 18 was obtained at the bottom of the tower. The second $C_3$+mixed alcohol flow 18 entered a propyl alcohol removal tower T8; under the condition where the number of theoretical plates of the propyl alcohol removal tower T8 was 20, the reflux ratio was 1 and the feed location was the 10th plate from the top, the tower top operation pressure was controlled to 0.05 MPaG, the tower top temperature was controlled to 100° C., and the tower bottom temperature was controlled to 140° C.; an n-propyl alcohol and 2-butanol mixture flow 19 was obtained at the top of the tower; and a $C_4$+mixed alcohol flow 20 was obtained at the bottom of the tower. The n-propyl alcohol and 2-butanol mixture flow 19 entered an n-propyl alcohol tower T9; under the condition where ethylene glycol was used as an extractant, the number of theoretical plates of the n-propyl alcohol tower T9 was 20, the reflux ratio was 1, the feed location of the mixture flow was the 10th plate from the top, the feed location of the extractant was the 2nd plate from the top and the feed mass ratio of the extractant and the mixture flow was 1, the operation pressure was controlled to −0.09 MPaG, the tower top temperature was controlled to 60° C., and the tower bottom temperature was controlled to 140° C.; an n-propyl alcohol flow with a water content less than 30 wt % 21 was obtained at the top of the tower; and an extractant and 2-butanol mixture flow with a water content less than 30 wt % 22 was obtained at the bottom of the tower.

The extractant and 2-butanol mixture flow with the water content less than 30 wt % 22 entered a 2-butanol tower T10; under the condition where the number of theoretical plates of the 2-butanol tower T10 was 20, the feed location was the 10th plate from the top and the reflux ratio was 1, the tower top operation pressure was controlled to −0.09 MPaG, the tower top temperature was controlled to 50° C., and the tower bottom temperature was controlled to 140° C.; a 2-butanol product flow with a purity of 99.51% 23 was obtained at the top of the tower; and a regenerative extractant flow with a water content less than 30 wt % 24 was obtained at the bottom of the tower and was returned into the n-propyl alcohol tower T9 for circulation.

Embodiment 5

A method for treating oxygenated volatile organic compounds in Fischer-Tropsch synthesis reaction water in this embodiment was implemented according to the process shown in FIG. 1, organic components of a Fischer-Tropsch synthesis reaction water flow 1 were changed, and operation conditions of all units were set as follows. Particularly, the Fischer-Tropsch synthesis reaction water flow 1 (see Table 1 for the components) entered a concentration tower T1; under the condition where the number of theoretical plates of the concentration tower T1 was 50, the reflux ratio was 10 and the feed location was the 45th plate from the top, the tower top operation pressure was controlled to 0.05 MPaG, the tower top temperature was controlled to 100° C., and the tower kettle temperature was controlled to 160° C.; a Fischer-Tropsch synthesis water flow with a water content less than 30 wt % 2 was extracted from the top of the tower, wherein the water content was 22% in this embodiment; and an acid-containing water flow 3 was extracted from the bottom of the tower.

The Fischer-Tropsch synthesis water flow with the water content less than 30 wt % 2 was preheated together with hydrogen and then entered a fixed bed hydrogenation reactor R filled with a catalyst by three sections, wherein in this embodiment, the mass ratio of all components of the catalyst met Zn:Cu:Al:Mg:Fe=35:28:8:0:0. Under the reaction condition where the reaction temperature was 250° C., the pressure was 5 MPa, the liquid space velocity was 3 h-1, and the molar ratio of hydrogen and carbonyl was 30, all aldehyde-ketone-acid-ester carbonyl compounds in the Fischer-Tropsch synthesis water flow with the water content less than 30 wt % 2 were converted into alcohols, so that a mixed-alcohol water solution flow 4 was obtained. The mixed-alcohol water solution flow 4 entered a carbonyl compound cutting tower T2; under the condition where the number of theoretical plates of the carbonyl compound cutting tower T2 was 100, the reflux ratio was 10 and the feed location was the 90th plate from the top, the tower top pressure was controlled to 0.05 MPaG, the tower top temperature was controlled to 90° C., and the tower bottom temperature was controlled to 110° C.; an aldehyde-ketoneester-rich flow 5 was obtained at the top of the tower and was returned into the hydrogenation reactor R for cyclic hydrogenation; and a mixed-alcohol water flow 6 was obtained at the bottom of the tower.

The mixed-alcohol water flow 6 entered a mixed-alcohol dehydration tower T3 which adopted benzene as an entrainer; under the condition where the number of theoretical plates of the mixed-alcohol dehydration tower T3 was 60 and the feed location was the 50th plate from the top, the tower top operation pressure was controlled to 0.05 MPaG, the tower top temperature was controlled to 90° C., and the tower bottom temperature was controlled to 120° C.; a tower top steam flow 7 was condensed and then entered a liquid-liquid separator F; an upper oil-phase flow 8 flowed back; a lower water-phase was extracted as a lower water-phase flow 9; and an anhydrous mixed alcohol flow 10 was obtained at the bottom of the tower.

The lower water-phase flow 9 entered a solvent recovery tower T4; under the condition where the number of theoretical plates of the solvent recovery tower T4 was 60, the reflux ratio was 8 and the feed location was the 50th plate from the top, the tower top operation pressure was controlled to 0.05 MPaG, the tower top temperature was controlled to 90° C., and the tower bottom temperature was controlled to 125° C.; a regenerative solvent flow 11 was obtained at the top of the tower; and a waste water flow 12 was obtained at the bottom of the tower. The anhydrous mixed alcohol flow 10 entered an ethyl alcohol tower T5; under the condition where the number of theoretical plates of the ethyl alcohol tower T5 was 150, the feed location is the 130th plate from the top and the reflux ratio was 15, the tower top operation pressure was controlled to −0.05 MPaG, the tower top temperature was controlled to 70° C., and the tower bottom temperature was controlled to 110° C.; a crude ethyl alcohol product flow 13 was obtained at the top of the tower; and a C$_3$+mixed alcohol flow 14 was obtained at the bottom of the tower. The crude ethyl alcohol product flow 13 entered an ethyl alcohol refining tower T6; under the condition where the number of theoretical plates of the ethyl alcohol refining tower T6 was 150, the feed location was the 130th plate from the top and the reflux ratio was 15, the tower top pressure was controlled to 0.05 MPaG, the tower top temperature was controlled to 100° C., and the tower bottom temperature was controlled to 110° C.; a methyl alcohol-rich flow 15 was obtained at the top of the tower; and an ethyl alcohol product flow 16 with a purity of 99.44% was obtained at the bottom of the tower.

The C$_3$+mixed alcohol flow 14 entered an isopropanol tower T7; under the condition where the number of theoretical plates of the isopropanol tower T7 was 100, the reflux ratio was 15 and the feed location was the 80th plate from the top, the tower top operation pressure was controlled to 0.05 MPaG, the tower top temperature was controlled to 105° C., and the tower bottom temperature was controlled to 130° C.; an isopropanol product flow 17 with a purity of 99.7% was obtained at the top of the tower, and a second C$_3$+mixed alcohol flow 18 was obtained at the bottom of the tower. The second C$_3$+mixed alcohol flow 18 entered a propyl alcohol removal tower T8; under the condition where the number of theoretical plates of the propyl alcohol removal tower T8 was 80, the reflux ratio was 10 and the feed location was the 70th plate from the top, the tower top operation pressure was controlled to 0.05 MPaG, the tower top temperature was controlled to 120° C., and the tower bottom temperature was controlled to 160° C.; an n-propyl alcohol and 2-butanol mixture flow 19 was obtained at the top of the tower; and a C$_4$+mixed alcohol flow 20 was obtained at the bottom of the tower. The n-propyl alcohol and 2-butanol mixture flow 19 entered an n-propyl alcohol tower T9; under the condition where ethylene glycol was used as an extractant, the number of theoretical plates of the n-propyl alcohol tower T9 was 80, the reflux ratio was 10, the feed location of the mixture flow was the 70th plate from the top, the feed location of the extractant was the 10th plate from the top and the feed mass ratio of the extractant and the mixture was 10, the operation pressure was controlled to −0.05 MPaG, the tower top temperature was controlled to 80° C., and the tower bottom temperature was controlled to 170° C.; an n-propyl alcohol flow with a purity of 99.52% and a water content less than 30 wt % 21 was obtained at the top of the tower; and an extractant and 2-butanol mixture flow with a water content less than 30 wt % 22 was obtained at the bottom of the tower. The extractant and 2-butanol mixture flow with the water content less than 30 wt % 22 entered a 2-butanol tower T10; under the condition where the number of theoretical plates of the 2-butanol tower T10 was 80, the feed location was the 70th plate from the top and the reflux ratio was 10, the tower top operation pressure was controlled to −0.09 MPaG, the tower top temperature was controlled to 80° C., and the tower bottom temperature was controlled to 175° C.; a 2-butanol product flow with the purity of 99.51% 23 was obtained at the top of the tower; and a regenerative extractant flow with a water content less than 30 wt % 24 was obtained at the bottom of the tower and was returned into the n-propyl alcohol tower T9 for circulation.

In the description of the invention, reference terms such as "an embodiment", "example" and "specific example" are intend to indicate that specific characteristics, structures, materials or features depicted in conjunction with the embodiment or example are included in at least one embodiment or example of the invention. In this specification, illustrative statements of these terms do not definitely refer to identical embodiments or examples. Moreover, the specific characteristics, structures, materials or features depicted by these terms can be properly combined in any one or more embodiments or examples.

The above description of the embodiments is meant to assist those ordinarily skilled in the art in the interpretation and application of the invention. Clearly, any skilled in the art can easily make different modifications to these embodiments and apply the basic principle of the invention to other embodiments without creative labor. Therefore, the invention is not limited to the above embodiments, and all improvements and modifications achieved by those skilled in the art without deviating from the scope of the invention should also fall within the protection scope of the invention.

What is claimed is:

1. A method for treating oxygenated volatile organic compounds in Fischer-Tropsch synthesis reaction water, comprising:
   (a) enabling a Fischer-Tropsch synthesis reaction water flow to enter a concentration tower, so that a Fischer-Tropsch synthesis water flow with a water content less than 30 wt % is obtained at a top of the tower, and an acid-containing water flow is obtained at a bottom of the concentration tower;
   (b) enabling the Fischer-Tropsch synthesis water flow with the water content less than 30 wt % to enter a hydrogenation reactor to convert all aldehyde-ketone-acid-ester carbonyl compounds in the flow into alcohols by hydrogenation, so that a mixed-alcohol water solution flow is obtained;
   (c) enabling the mixed-alcohol water solution flow to enter a carbonyl compound cutting tower to separate carbonyl compounds that are not completely reacted from the alcohols, so that an aldehyde-ketone-ester-rich flow is obtained at a top of the tower and is returned into the hydrogenation reactor for cyclic hydrogenation, and a mixed-alcohol water flow is obtained at a bottom of the tower;

(d) enabling the mixed-alcohol water flow to enter a mixed-alcohol dehydration tower, condensing a tower top steam flow, then enabling the condensed tower top steam flow to enter a liquid-liquid separator, returning an upper oil-phase flow into the mixed-alcohol dehydration tower for circulation, extracting a lower water-phase flow, and extracting an anhydrous mixed alcohol flow from a bottom of the tower;

(e) enabling the lower water-phase flow to enter a solvent recovery tower, so that a regenerative entrainer flow is obtained at a top of the tower and returns into the mixed-alcohol dehydration tower, and a waste water flow is extracted from a bottom of the tower and is discharged;

(f) enabling the anhydrous mixed alcohol flow to enter an ethyl alcohol tower, so that a crude ethyl alcohol product flow is obtained at a top of the tower, and a $C_3$+mixed alcohol flow is obtained at a bottom of the tower;

(g) enabling the crude ethyl alcohol product flow to enter an ethyl alcohol refining tower, so that a methyl alcohol-rich flow is obtained at a top of the tower, and an ethyl alcohol product flow is obtained at a bottom of the tower;

(h) enabling the $C_3$+mixed alcohol flow to enter an isopropanol tower, so that an isopropanol product flow is obtained at a top of the tower, and a second $C_3$+mixed alcohol flow is obtained at a bottom of the tower;

(i) enabling the second $C_3$+mixed alcohol flow to enter a propyl alcohol removal tower, so that an n-propyl alcohol and 2-butanol mixture flow is extracted from a top of the tower, and a $C_4$+mixed alcohol flow is obtained at a bottom of the tower;

(j) enabling the n-propyl alcohol and 2-butanol mixture flow to enter an n-propyl alcohol tower to reversely make contact with an extractant flow entering the tower from the top, so that an n-propyl alcohol flow is extracted from a top of the tower, and an extractant and 2-butanol mixture flow is extracted from a bottom of the tower; and (k) enabling the extractant and 2-butanol mixture flow to enter a 2-butanol tower, so that a 2-butanol product flow is obtained at a top of the tower, and a regenerative extractant flow is obtained at a bottom of the tower and is returned into the n-propyl alcohol tower for circulation.

2. The method for treating oxygenated volatile organic compounds in Fischer-Tropsch synthesis reaction water according to claim 1, wherein a hydrogenation catalyst adopted by the hydrogenation reactor includes Zn, Cu, Al, Mg and Fe, wherein the mass ratio of Zn, Cu, Al, Mg and Fe is 10-55:15-60:0.1-10:0-1:0-1.

3. The method for treating oxygenated volatile organic compounds in Fischer-Tropsch synthesis reaction water according to claim 1, wherein the Fischer-Tropsch synthesis water flow with the water content less than 30 wt % is a $C_1$-$C_8$ alcohol-aldehyde-ketone-acid-ester mixture water solution, and in the hydrogenation reactor, all aldehyde-ketone-acid-ester carbonyl compounds in the flow are converted into alcohols.

4. The method for treating oxygenated volatile organic compounds in Fischer-Tropsch synthesis reaction water according to claim 1, wherein the hydrogenation reactor is a multi-filled fixed bed reactor; and before entering the reactor, a mixed flow of the Fischer-Tropsch synthesis water flow and hydrogen is preheated to 190-220° C., a reaction product is condensed to 20-50° C., and an oxygenated volatile organic compound water solution is separated from the hydrogen.

5. The method for treating oxygenated volatile organic compounds in Fischer-Tropsch synthesis reaction water according to claim 1, wherein the hydrogenation reactor has a hydrogenation reaction temperature of 200-250° C., a pressure of 1-5 MPa, a liquid space velocity of 0.2-3 h$^{-1}$, and a hydrogen-carbonyl ratio of 5-30.

6. The method for treating oxygenated volatile organic compounds in Fischer-Tropsch synthesis reaction water according to claim 1, wherein the mixed-alcohol dehydration tower is an azeotropic distillation tower and adopts an entrainer which is one or a mixture of more than one of benzene, methylbenzene, cyclohexane, n-hexane and ethyl acetate.

7. The method for treating oxygenated volatile organic compounds in Fischer-Tropsch synthesis reaction water according to claim 6, wherein the entrainer is benzene.

8. The method for treating oxygenated volatile organic compounds in Fischer-Tropsch synthesis reaction water according to claim 1, wherein the ethyl alcohol tower is a vacuum distillation tower.

9. The method for treating oxygenated volatile organic compounds in Fischer-Tropsch synthesis reaction water according to claim 1, wherein the n-propyl alcohol tower is an extractive distillation tower and adopts an extractant which is one or a mixture of more than one of ethylene glycol, 1,3-propylene glycol and 1,2-propylene glycol.

10. The method for treating oxygenated volatile organic compounds in Fischer-Tropsch synthesis reaction water according to claim 1, wherein the number of theoretical plates of the concentration tower is 20-50, a feed location is the 5th-45th plate from the top, a reflux ratio is 1-10, a tower top pressure is controlled to a normal pressure, a tower top temperature is 70-100° C., and a tower kettle temperature is 80-160° C.;

the number of theoretical plates of the carbonyl compound cutting tower is 20-100, a reflux ratio is 2-10, a feed location is the 5th-90th plate from the top, a tower top pressure is controlled to a normal pressure, a tower top temperature is 65-90° C., and a tower bottom temperature is 85-110° C.;

the number of theoretical plates of the mixed alcohol hydration tower is 15-60, a feed location is the 5th-50th plate from the top, a tower top pressure is controlled to a normal pressure, a tower top temperature is 50-90° C., and a tower kettle temperature is 80-120° C.;

the number of theoretical plates of the solvent recovery tower is 10-60, a feed location is the 3rd-50th plate from the top, a reflux ratio is 0.5-8, a tower top pressure is controlled to a normal pressure, a tower top temperature is 45° C.-90° C., and a tower kettle temperature is 90° C.-125° C.;

the number of theoretical plates of the ethyl alcohol tower is 30-150, a reflux ratio is 3-15, a feed location is the 10th-130th plate from the top, a tower top pressure is controlled to −0.5-0.9 bar by a pressure reduction operation, a tower top temperature is 30° C.-70° C., and a tower bottom temperature is 55° C.-110° C.;

the number of theoretical plates of the ethyl alcohol refining tower is 20-150, a reflux ratio is 3-15, a feed location is the 10th-130th plate from the top, a top pressure of the refining tower is controlled to a normal temperature, a tower top temperature is 60-100° C., and a tower bottom temperature is 80° C.-110° C.;

the number of theoretical plates of the isopropanol tower is 20-100, a reflux ratio is 1-15, a feed location is the 10th-70th plate from the top, a tower top pressure is controlled to a normal temperature, a tower top temperature is 80-105° C., and a tower bottom temperature is 110° C.-130° C.;

the number of theoretical plates of the propyl alcohol tower is 20-80, a reflux ratio is 1-10, a feed location is the 10th-70th plate, a top pressure of the propyl alcohol tower is controlled to a normal temperature, a tower top temperature is 100-120° C., and a tower bottom temperature is 140° C.-160° C.;

the number of theoretical plates of the propyl alcohol tower is 20-80, a reflux ratio is 1-10, a feed location of a solvent is the 2nd-10th plate, a feed location of the n-propyl alcohol and 2-butanol mixture flow is the 10th-70th plate, the feed mass ratio of the solvent and the mixture flow is 1-10, a top pressure of the propyl alcohol tower is controlled to −0.09~−0.05 MPaG, a tower top temperature is 60-80° C., and a tower bottom temperature is 140° C.-170° C.; and the number of theoretical plates of the 2-butanol tower is 20-80, a reflux ratio is 1-10, a feed location is the 10th-70th plate, a tower top operation pressure is controlled to −0.09~−0.05 MPaG, tower top temperature is 50-80° C., and a tower bottom temperature is 140-175° C.

11. The method for treating oxygenated volatile organic compounds in Fischer-Tropsch synthesis reaction water according to claim 1, wherein the extractant is ethylene glycol.

* * * * *